(12) United States Patent  (10) Patent No.: US 9,179,677 B2
Ammermann et al.  (45) Date of Patent: Nov. 10, 2015

(54) FUNGICIDAL MIXTURES BASED ON PROTHIOCONAZOLE

(75) Inventors: Eberhard Ammermann, Heppenheim (DE); Reinhard Stierl, Freinsheim (DE); Gisela Lorenz, Neustadt (DE); Siegfried Strathmann, Limburgerhof (DE); Klaus Schelberger, Gönnheim (DE); V. James Spadafora, Sugar Land, TX (US); Thomas Christen, Dannstadt-Schauernheim (DE)

(73) Assignee: BASF AKTIENGESELLSCHAFT, Ludwigshafen (DE)

( * ) Notice: Subject to any disclaimer, the term of this patent is extended or adjusted under 35 U.S.C. 154(b) by 2195 days.

(21) Appl. No.: 10/505,708

(22) PCT Filed: Feb. 26, 2003

(86) PCT No.: PCT/EP03/01930
§ 371 (c)(1),
(2), (4) Date: Aug. 26, 2004

(87) PCT Pub. No.: WO03/073850
PCT Pub. Date: Sep. 12, 2003

(65) Prior Publication Data
US 2005/0107376 A1  May 19, 2005

(30) Foreign Application Priority Data
Mar. 1, 2002 (DE) .................. 102 08 841

(51) Int. Cl.
*A01N 43/64* (2006.01)
*A01N 43/653* (2006.01)
(Continued)

(52) U.S. Cl.
CPC .............. *A01N 43/653* (2013.01); *A01N 43/40* (2013.01); *A01N 43/84* (2013.01); *A01N 2300/00* (2013.01)

(58) Field of Classification Search
CPC . A01N 43/653; A01N 2300/00; A01N 43/40; A01N 43/84
See application file for complete search history.

(56) References Cited

U.S. PATENT DOCUMENTS 4,202,894 A  5/1980  Pfiffner
4,241,058 A  12/1980  Pfiffner
5,229,357 A  7/1993  Seele et al.
(Continued)

FOREIGN PATENT DOCUMENTS

EP   425 857    5/1991
EP   683 980   11/1995
(Continued)

OTHER PUBLICATIONS alanwood.net, 11 pages.*
(Continued)

*Primary Examiner* — Kyle Purdy
(74) *Attorney, Agent, or Firm* — Novak Druce Connolly Bove + Quigg LLP

(57) ABSTRACT

A fungicidal mixture comprising
(1) 2-[2-(1-chlorocyclopropyl)-3-(2-chlorophenyl)-2-hydroxy-propyl]-2,4-dihydro-[1,2,4]-triazole-3-thione (prothioconazole) of the formula I or a salt or adduct thereof

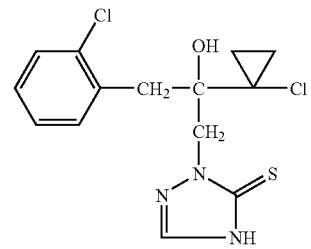

and at least one further fungicide or a salt or adduct thereof selected from the group consisting of
(2) fenpropimorph of the formula II

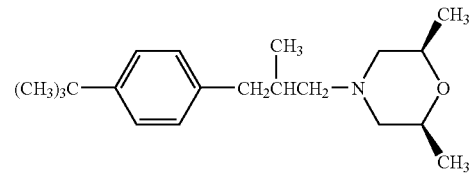

and
(3) tridemorph of the formula III

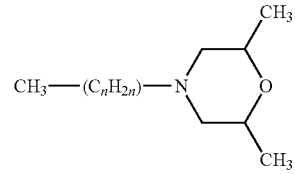

n=10, 11, 12 (60-70%) or 13
and
(4) fenpropidin of the formula IV

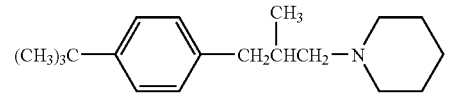

in a synergistically effective amount is described.

10 Claims, No Drawings

(51) Int. Cl.
*A01N 43/40* (2006.01)
*A01N 43/84* (2006.01)

(56) References Cited

U.S. PATENT DOCUMENTS

| | | | |
|---|---|---|---|
| 5,424,317 A | | 6/1995 | Kueng et al. |
| 5,521,195 A | | 5/1996 | Kueng |
| 5,789,430 A | | 8/1998 | Jautelat et al. |
| 5,859,039 A | | 1/1999 | Jautelat et al. |
| 5,880,143 A | * | 3/1999 | Goettsche et al. ............ 514/383 |
| 6,306,850 B1 | * | 10/2001 | Dutzmann et al. ......... 514/229.2 |
| 2002/0173529 A1 | | 11/2002 | Dutzmann et al. |
| 2003/0161896 A1 | * | 8/2003 | Mauler-Machnik et al. . 424/705 |

FOREIGN PATENT DOCUMENTS

| | | |
|---|---|---|
| EP | 727 142 | 8/1996 |
| WO | 96/16048 | 5/1996 |
| WO | 98/47367 | 10/1998 |
| WO | 00/63188 A1 | 10/2000 |

OTHER PUBLICATIONS

"Fungizide Kombination spraparate", Research Disclosure, Kenneth Mason, XP 000084558.

English language abstract and machine translation of WO 00/63188 A1, published Oct. 26, 2000.

* cited by examiner

FUNGICIDAL MIXTURES BASED ON PROTHIOCONAZOLE

The present invention relates to fungicidal mixtures, comprising (1) 2-[2-(1-chlorocyclopropyl)-3-(2-chlorophenyl)-2-hydroxy-propyl]-2,4-dihydro-[1,2,4]-triazole-3-thione (prothioconazole) of the formula I or a salt or adduct thereof

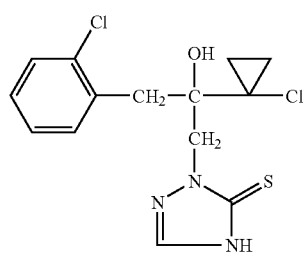

(I)

and at least one further fungicide or a salt or adduct thereof selected from the group consisting of (2) fenpropimorph of the formula II

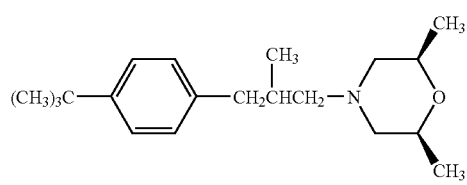

(II)

and (3) tridemorph of the formula III

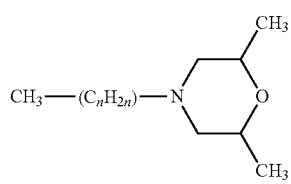

(III)

n=10, 11, 12 (60-70%) or 13 and (4) fenpropidin of the formula IV

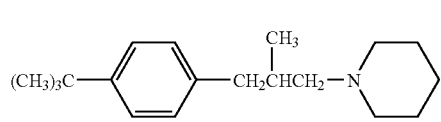

(IV)

in a synergistically effective amount.

Moreover, the invention relates to a method for controlling harmful fungi using mixtures of the compound I with at least one of the compounds II, III or IV and to the use of the compounds I, II, III and IV for preparing such mixtures, and also to compositions comprising these mixtures.

The compound of the formula I, 2-[2-(1-chlorocyclopropyl)-3-(2-chlorophenyl)-2-hydroxypropyl]-2,4-dihydro-[1,2,4]-triazole-3-thione (prothioconazole) is already known from WO 96/16048.

WO 98/47367 discloses a number of active compound combinations of prothioconazole with a large number of other fungicidal compounds.

Fenpropimorph of the formula II and its use as crop protection agent are described in DE-A-2 752 135.

Tridemorph of the formula III is likewise known and is described in DE-A-1 164 152.

Finally, fenpropidin of the formula IV, too, is known, and it is described in DE-A-2 752 096.

It is an object of the present invention to provide mixtures which have an improved activity against harmful fungi combined with a reduced total amount of active compounds applied (synergistic mixtures), with a view to reducing the application rates and improving the activity spectrum of the known compounds I, II, III and IV.

We have found that this object is achieved by the mixture, defined at the outset, of prothioconazole with at least one further fungicide. Moreover, we have found that applying the compound I and at least one further compound II, III or IV simultaneously, i.e. together or separately, or applying the compound I and at least one of the compounds II, III or IV in succession provides better control of harmful fungi than is possible with the individual compounds alone.

2-[2-(1-Chlorocyclopropyl)-3-(2-chlorophenyl)-2-hydroxypropyl]-2,4-dihydro-[1,2,4]-triazole-3-thione of the formula I is known from WO 96-16 048. The compound can be present in the "thiono" form of the formula

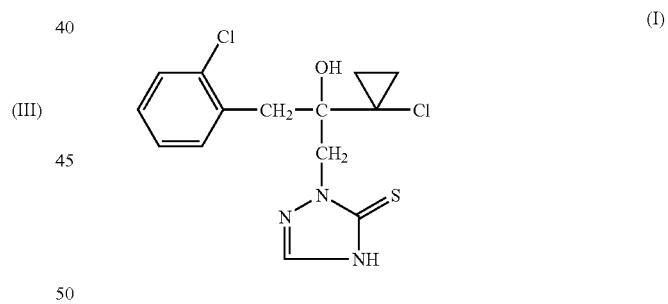

(I)

or in the tautomeric "mercapto" form of the formula

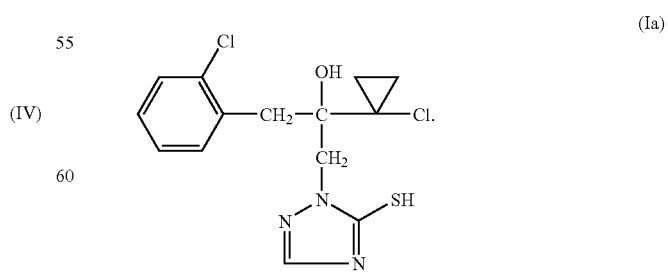

(Ia)

For the sake of simplicity, only the "thiono" form is shown in each case.

Fenpropimorph of the formula II

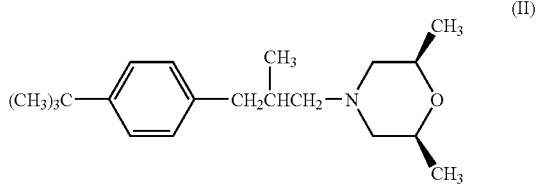

is known from DE-A-2 752 135.

Tridemorph of the formula III

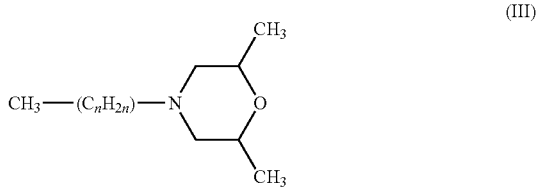

n=10, 11, 12 (60-70%) or 13
is described in DE-A-1 164 125.

Fenpropidin of the formula IV

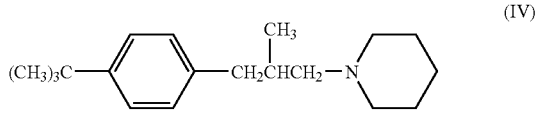

is known from DE-A-2 752 096.

Owing to the basic character of their nitrogen atoms, the compounds I to IV are capable of forming salts or adducts with inorganic or organic acids or with metal ions.

Examples of inorganic acids are hydrohalic acids, such as hydrogen fluoride, hydrogen chloride, hydrogen bromide and hydrogen iodide, carbonic acid, sulfuric acid, phosphoric acid and nitric acid.

Suitable organic acids are, for example, formic acid, and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or -disulfonic acids (aromatic radicals, such as phenyl and naphthyl, which carry one or two sulfonic acid groups), alkylphosphonic acids (phosphonic acids having straight-chain or branched alkyl radicals of 1 to 20 carbon atoms), arylphosphonic acids or -diphosphonic acids (aromatic radicals, such as phenyl and naphthyl, which carry one or two phosphonic acid radicals), where the alkyl and/or aryl radicals may carry further substituents, for example p-toluenesulfonic acid, salicylic acid, p-aminosalicylic acid, 2-phenoxybenzoic acid, 2-acetoxybenzoic acid, etc.

Suitable metal ions are in particular the ions of the elements of the second main group, in particular calcium and magnesium, of the third and fourth main group, in particular aluminum, tin and lead, and of the first to eighth transition group, in particular chromium, manganese, iron, cobalt, nickel, copper, zinc and others. Particular preference is given to the metal ions of the elements of the transition groups of the fourth period. The metals can be present in the various valencies which they can assume.

Preference is given to mixtures of prothioconazole with fenpropimorph.

Furthermore, preference is also given to mixtures of prothioconazole with tridemorph.

Preference is also given to mixtures of prothioconazole with fenpropidin.

Preference is also given to ternary mixtures of prothioconazole with two of the abovementioned fungicides.

When preparing the mixtures, it is preferred to employ the pure active compounds I, II, III and IV, to which can be added further active compounds against harmful fungi or against other pests, such as insects, arachnids or nematodes, or else herbicidal or growth-regulating active compounds or fertilizers.

The mixtures of the compound I with at least one of the compounds II, III or IV, or the compound I and at least one of the compounds II, III and IV used simultaneously, jointly or separately, exhibit outstanding activity against a wide range of phytopathogenic fungi, in particular from the classes of the Ascomycetes, Basidiomycetes, Phycomycetes and Deuteromycetes. Some of them act systemically and can therefore be employed as foliar- and soil-acting fungicides.

They are especially important for controlling a large number of fungi in a variety of crop plants, such as cotton, vegetable species (e.g. cucumbers, beans, tomatoes, potatoes and cucurbits), barley, grass, oats, bananas, coffee, corn, fruit species, rice, rye, soya, grapevine, wheat, ornamentals, sugar cane, and a variety of seeds.

They are particularly suitable for controlling the following phytopathogenic fungi: *Blumeria graminis* (powdery mildew) in cereals, *Erysiphe cichoracearum* and *Sphaerotheca fuliginea* in cucurbits, *Podosphaera leucotricha* in apples, *Uncinula necator* in grapevines, *Puccinia* species in cereals, *Rhizoctonia* species in cotton, rice and lawns, *Ustilago* species in cereals and sugar cane, *Venturia inaequalis* (scab) in apples, *Helminthosporium* species in cereals, *Septoria nodorum* in wheat, *Botrytis cinera* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, *Plasmopara viticola* in grapevines, *Pseudoperonospora* species in hops and cucumbers, *Alternaria* species in vegetables and fruit, *Mycosphaerella* species in bananas and *Fusarium* and *Verticillium* species.

They can furthermore be employed in the protection of materials (for example the protection of wood), for example against *Paecilomyces variotii*.

The compound I and at least one of the compounds II, III and IV can be applied simultaneously, that is either together or separately, or successively, the sequence, in the case of separate application, generally not having any effect on the result of the control measures.

The compounds I and II are usually applied in a weight ratio of from 20:1 to 1:20, in particular from 10:1 to 1:10, preferably from 5:1 to 1:5.

The compounds I and III are usually applied in a weight ratio of from 20:1 to 1:20, in particular from 10:1 to 1:10, preferably from 5:1 to 1:5.

The compounds I and IV are usually applied in a weight ratio of from 20:1 to 1:20, in particular from 10:1 to 1:10, preferably from 5:1 to 1:5.

Depending on the kind of effect desired, the application rates of the mixtures according to the invention are, in particular in agricultural crop areas, from 0.01 to 8 kg/ha, preferably from 0.1 to 5 kg/ha, in particular from 0.1 to 3.0 kg/ha.

The application rates of the compounds I are from 0.01 to 1 kg/ha, preferably from 0.05 to 0.5 kg/ha, in particular from 0.05 to 0.3 kg/ha.

Correspondingly, the application rates for the compounds II are from 0.01 to 1 kg/ha, preferably from 0.02 to 0.5 kg/ha, in particular from 0.05 to 0.3 kg/ha.

Correspondingly, the application rates for the compounds III are from 0.01 to 1 kg/ha, preferably from 0.02 to 0.5 kg/ha, in particular from 0.05 to 0.3 kg/ha.

Correspondingly, the application rates for the compounds IV are from 0.01 to 1 kg/ha, preferably from 0.02 to 0.5 kg/ha, in particular from 0.05 to 0.3 kg/ha.

For seed treatment, the application rates of the mixture are generally from 0.001 to 250 g/kg of seed, preferably 0.01 to 100 g/kg, in particular 0.01 to 50 g/kg.

If phytopathogenic harmful fungi are to be controlled, the separate or joint application of the compound I and at least one of the compounds II, III and IV or of the mixtures of the compound I and at least one of the compounds II, III and IV is effected by spraying or dusting the seeds, the plants or the soils before or after sowing of the plants, or before or after plant emergence.

The fungicidal synergistic mixtures according to the invention or the compound I and at least one of the compounds II, III and IV can be formulated for example in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should ensure as fine and uniform as possible a distribution of the mixture according to the invention.

The formulations are prepared in a known manner, e.g. by adding solvents and/or carriers. The formulations are usually admixed with inert additives, such as emulsifiers or dispersants.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenyl ether, ethoxylated isooctyl-, octyl- or nonylphenol, alkylphenol or tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, lignosulfite waste liquors or methylcellulose.

Powders, materials for broadcasting and dusts can be prepared by mixing or jointly grinding the compound I and at least one of the compounds II, III and IV or the mixture of the compound I and at least one of the compounds II, III and IV with a solid carrier.

Granules (e.g. coated granules, impregnated granules or homogeneous granules) are usually prepared by binding the active compound, or active compounds, to a solid carrier.

Fillers or solid carriers are, for example, mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably 0.5 to 90% by weight, of compound I and at least one of the compounds II, III and IV or of the mixture of compound I and at least one of the compounds II, III and IV. The active compounds are employed in a purity of from 90% to 100%, preferably 95% to 100% (according to NMR spectrum or HPLC).

The compounds I, II, III and IV of the mixtures, or the corresponding formulations, are applied by treating the harmful fungi, their habitat, or the plants, seeds, soils, areas, materials or spaces to be kept free from them with a fungicidally effective amount of the mixture, or of the compound I and at least one of the compounds II, III and IV in the case of separate application.

Application can be effected before or after infection by the harmful fungi.

USE EXAMPLE

The synergistic activity of the mixtures according to the invention was demonstrated by the following experiments:

The active compounds, separately or together, were formulated as a 10% emulsion in a mixture of 63% by weight of cyclohexanone and 27% by weight of emulsifier, and diluted with water to the desired concentration.

Evaluation was carried out by determining the infected leaf areas in percent. These percentages were converted into efficacies. The efficacy (W) was calculated as follows using Abbot's formula:

$$W = \left(1 - \frac{\alpha}{\beta}\right) \cdot 100$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active compounds were determined using Colby's formula [R. S. Colby, Weeds 15, 20-22 (1967)] and compared with the observed efficacies.

$E = x + y - x \cdot y / 100$    Colby's formula:

E expected efficacy, expressed in % of the untreated control, when using the mixture of the active compounds A and B at the concentrations a and b x efficacy, expressed in % of the untreated control, when using active compound A at a concentration of a y efficacy, expressed in % of the untreated control, when using active compound B at a concentration of b.

Use Example 1

Activity Against Mildew of Wheat Caused by
*Erysiphe* [syn. *Blumeria*] *graminis* forma specialis.
tritici Leaves of wheat seedlings of the cultivar "Kanzler", which had been grown in pots, were sprayed to runoff point with an aqueous suspension having the concentration of active compound stated below. The suspension or emulsion was prepared from a stock solution with 10% of active compound in a mixture comprising 85% of cyclohexanone and 5% of emulsifier. 24 hours after the spraycoating had dried on, the plants were dusted with spores of mildew of wheat (*Erysiphe* [syn. *Blumeria*] *graminis* forma specialis. tritici). The test plants were then placed in a greenhouse at 20-24° C. and 60-90% relative atmospheric humidity. After 7 days, the extent of the mildew development was determined visually in % infection of the total leaf area.

The visually determined values for the percentage of diseased leaf areas were converted into efficacies in % of the untreated control. An efficacy of 0 means the same disease level as in the untreated control, an efficacy of 100 means 0% disease. The expected efficacies for combinations of active compounds were determined using the abovementioned Colby formula and compared with the observed efficacies.

TABLE 1

| Active compound | Concentration of active compound in the spray liquor in ppm | Efficacy in % of the untreated control |
|---|---|---|
| Control (untreated) | (77% infestation) | 0 |
| Compound I = prothioconazole | 1 | 0 |
|  | 0.25 | 0 |
| Compound II = fenpropimorph | 2.5 | 74 |
|  | 0.6 | 0 |
|  | 0.15 | 0 |
| Compound III = tridemorph | 2.5 | 48 |
|  | 0.6 | 0 |
|  | 0.15 | 0 |
| Compound IV = fenpropidin | 0.6 | 61 |
|  | 0.15 | 0 |

TABLE 2

| Combinations according to the invention | Observed efficacy | Calculated efficacy* |
|---|---|---|
| Compound I = prothioconazole + compound II = fenpropimorph 0.25 + 2.5 ppm mixture 1:10 | 87 | 74 |
| Compound I = prothioconazole + compound II = fenpropimorph 1 + 2.5 ppm mixture 1:2.5 | 87 | 74 |
| Compound I = prothioconazole + compound II = fenpropimorph 0.25 + 0.6 ppm mixture 1:2.5 | 35 | 0 |
| Compound I = prothioconazole + compound II = fenpropimorph 1 + 0.6 ppm mixture 1:1.6 | 74 | 0 |
| Compound I = prothioconazole + compound II = fenpropimorph 0.25 + 0.15 ppm mixture 1:1.6 | 48 | 0 |
| Compound I = prothioconazole + compound III = tridemorph 0.25 + 2.5 ppm mixture 1:10 | 61 | 48 |
| Compound I = prothioconazole + compound III = tridemorph 1 + 2.5 ppm mixture 1:2.5 | 99 | 48 |
| Compound I = prothioconazole + compound III = tridemorph 0.25 + 0.6 ppm mixture 1:2.5 | 61 | 0 |
| Compound I = prothioconazole + compound III = tridemorph 1 + 0.6 ppm mixture 1:1.6 | 74 | 0 |
| Compound I = prothioconazole + compound III = tridemorph 0.25 + 0.15 ppm mixture 1:1.6 | 87 | 0 |
| Compound I = prothioconazole + compound IV = fenpropidin 0.25 + 0.6 ppm mixture 1:2.5 | 100 | 61 |

The test results show that in all mixing ratios the observed efficacy is higher than the efficacy calculated beforehand using Colby's formula (from Synerg 172.XLS).

Use Example 2

Curative Activity Against Brown Rust of Wheat Caused by *Puccinia recondita*

Leaves of wheat seedlings of the cultivar "Kanzler", which had been grown in pots, were dusted with spores of brown rust (*Puccinia recondita*). The pots were then placed in a chamber with high atmospheric humidity (90-95%), at 20-22° C. During this time, the spores germinated and the germinal tubes penetrated into the leaf tissue. The next day, the infected plants were sprayed to runoff point with an aqueous suspension having the concentration of active compound stated below. The suspension or emulsion was prepared from a stock solution with 10% of active compound in a mixture comprising 85% of cyclohexanone and 5% of emulsifier. After the spray coating had dried on, the test plants were cultivated in a greenhouse at 20-22° C. in 65-70% relative atmospheric humidity for 7 days. The extent of the rust fungus development on the leaves was then determined.

The visually determined values for the percentage of diseased leaf areas were converted into efficacies in % of the untreated control. An efficacy of 0 means the same disease level as in the untreated control, an efficacy of 100 means 0% disease. The expected efficacies for active compound combinations were determined using the abovementioned Colby formula and compared with the observed efficacies.

TABLE 3

| Active compound | Concentration of active compound in the spray liquor in ppm | Efficacy in % of the untreated control |
|---|---|---|
| Control (untreated) | (90% infestation) | 0 |
| Compound I = prothioconazole | 1 | 78 |
|  | 0.25 | 22 |
| Compound II = fenpropimorph | 2.5 | 22 |
|  | 0.6 | 0 |
|  | 0.15 | 0 |
| Compound III = tridemorph | 2.5 | 0 |
|  | 0.6 | 0 |
|  | 0.15 | 0 |
| Compound IV = fenpropidin | 2.5 | 44 |
|  | 0.6 | 0 |
|  | 0.15 | 0 |

TABLE 4

| Combinations according to the invention | Observed efficacy | Calculated efficacy* |
|---|---|---|
| Compound I = prothioconazole + compound II = fenpropimorph 0.25 + 2.5 ppm mixture 1:10 | 55 | 44 |
| Compound I = prothioconazole + compound II = fenpropimorph 1 + 2.5 ppm mixture 1:2.5 | 92 | 83 |
| Compound I = prothioconazole + compound II = fenpropimorph 0.25 + 0.6 ppm mixture 1:2.5 | 44 | 22 |
| Compound I = prothioconazole + compound II = fenpropimorph 1 + 0.6 ppm mixture 1:1.6 | 94 | 78 |
| Compound I = prothioconazole + compound II = fenpropimorph 0.25 + 0.15 ppm mixture 1:1.6 | 44 | 22 |
| Compound I = prothioconazole + compound III = tridemorph 0.25 + 2.5 ppm mixture 1:10 | 44 | 22 |
| Compound I = prothioconazole + compound III = tridemorph 1 + 2.5 ppm mixture 1:2.5 | 92 | 78 |
| Compound I = prothioconazole + compound III = tridemorph 0.25 + 0.6 ppm mixture 1:2.5 | 44 | 22 |
| Compound I = prothioconazole + compound III = tridemorph 1 + 0.6 ppm mixture 1:1.6 | 89 | 78 |

TABLE 4-continued

| Combinations according to the invention | Observed efficacy | Calculated efficacy* |
|---|---|---|
| Compound I = prothioconazole + compound III = tridemorph 0.25 + 0.15 ppm mixture 1:1.6 | 44 | 22 |
| Compound I = prothioconazole + compound | 78 | 57 |

*)Efficacy calculated using Colby's formula

The test results show that in all mixing ratios the observed efficacy is higher than the efficacy calculated beforehand using Colby's formula (from Synerg 172.XLS).

We claim:

1. A fungicidal mixture, comprising a synergistic combination of components (a) and (b) wherein
   (a) is 2-[2-(1-chlorocyclopropyl)-3-(2-chlorophenyl)-2-hydroxy-propyl]-2,4-dihydro-[1,2,4]-triazole-3-thione (prothioconazole) of the formula I or a salt or adduct thereof

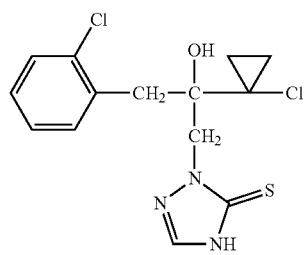

and
(b) is at least one further fungicide or a salt or adduct thereof selected from the group consisting of fenpropimorph of the formula II

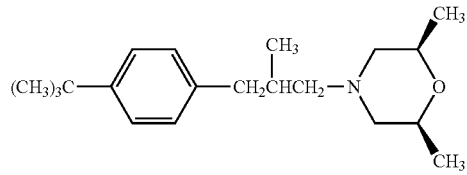

and tridemorph of the formula III

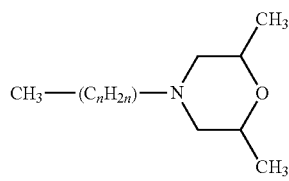

n=10, 11, 12 (60-70%) or 13
and fenpropidin of the formula IV

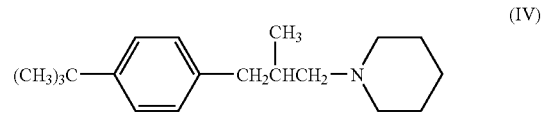

wherein components (a) and (b) are combined in synergistically effective amounts, and wherein components (a) and (b) are combined in a weight ratio such that the weight ratio of prothioconazole to fenpropimorph, if present, is from 20:1 to 1:20, the weight ratio of prothioconazole to tridemorph, if present, is from 20:1 to 1:20, and the weight ratio of prothioconazole to fenpropidin, if present, is from 20:1 to 1:20.

2. A fungicidal mixture as claimed in claim 1, comprising prothioconazole of the formula I and fenpropimorph of the formula II.

3. A fungicidal mixture as claimed in claim 1, comprising prothioconazole of the formula I and tridemorph of the formula III.

4. A fungicidal mixture as claimed in claim 1, comprising prothioconazole of the formula I and fenpropidin of the formula IV.

5. A fungicidal mixture as claimed in claim 1, wherein the weight ratio of prothioconazole to fenpropimorph, if present, is from 10:1 to 1:10, to tridemorph, if present, is from 10:1 to 1:10, and to fenpropidin, if present, is from 10:1 to 1:10.

6. A method for controlling harmful fungi, which comprises treating the harmful fungi, their habitat or the plants, seeds, soils, areas, materials or spaces to be kept free from them with a fungicidal mixture as claimed in claim 1.

7. A method as claimed in claim 6, wherein the synergistically effective amounts of the components (a) and (b) are applied simultaneously, that is either together or separately, or successively.

8. A method as claimed in claim 6, wherein the fungicidal mixture or the synergistically effective amounts of the components (a) and (b) is/are applied in an amount of from 0.01 to 8 kg/ha.

9. A fungicidal composition, comprising the fungicidal mixture as claimed in claim 1 and a solid or liquid carrier.

10. A fungicidal mixture as claimed in claim 1, wherein the weight ratio of prothioconazole to fenpropimorph, if present, is from 5:1 to 1:5, to tridemorph, if present, is from 5:1 to 1:5, and to to fenpropidin, if present, is from 5:1 to 1:5.

* * * * *